(12) United States Patent
Figge et al.

(10) Patent No.: US 8,389,250 B2
(45) Date of Patent: Mar. 5, 2013

(54) METHODS FOR PRODUCING METHIONINE BY CULTURING A MICROORGANISM MODIFIED TO ENHANCE PRODUCTION OF CYSTEINE

(75) Inventors: Rainer Figge, Riom (FR); Fabien Lux, Saint-Priest (FR); Céline Raynaud, Dallet (FR); Michel Chateau, Riom (FR); Philippe Soucaille, Deyme (FR)

(73) Assignee: Metabolic Explorer (FR)

( * ) Notice: Subject to any disclaimer, the term of this patent is extended or adjusted under 35 U.S.C. 154(b) by 65 days.

(21) Appl. No.: 12/159,846

(22) PCT Filed: Jan. 4, 2006

(86) PCT No.: PCT/EP2006/050033
§ 371 (c)(1),
(2), (4) Date: Jul. 1, 2008

(87) PCT Pub. No.: WO2007/077041
PCT Pub. Date: Jul. 12, 2007

(65) Prior Publication Data
US 2008/0311632 A1    Dec. 18, 2008

(51) Int. Cl.
*C12P 13/12* (2006.01)
*C12P 21/06* (2006.01)
*C12P 21/04* (2006.01)
*C12N 1/20* (2006.01)
*C12N 15/00* (2006.01)

(52) U.S. Cl. .................. 435/113; 435/252.3; 435/69.1; 435/71.1; 435/320.1

(58) Field of Classification Search .................. None
See application file for complete search history.

(56) References Cited

U.S. PATENT DOCUMENTS

| 6,831,165 | B1 * | 12/2004 | Pompejus et al. | 536/23.1 |
| 2003/0219881 | A1 * | 11/2003 | Brigitte et al. | 435/106 |
| 2005/0124049 | A1 | 6/2005 | Ziyatdinov et al. | |

FOREIGN PATENT DOCUMENTS

| EP | 1445310 A1 | 8/2004 |
| EP | 1 686 184 | 8/2006 |
| JP | 2005-137369 | 6/2005 |
| WO | WO 03/006666 A2 | 1/2003 |
| WO | WO 2004/057003 A2 | 7/2004 |
| WO | WO 2004/108894 A | 12/2004 |
| WO | WO 2005/059155 A2 | 6/2005 |
| WO | WO 2005/085463 A | 9/2005 |
| WO | WO 2005/090589 A2 | 9/2005 |
| WO | 2005/111202 A1 | 11/2005 |
| WO | WO 2006/082254 A | 8/2006 |

OTHER PUBLICATIONS

Nakamori et al., 1999, Appl. Microbiol. Biotechnol., 52: 179-185.*
Kumar et al., 2005, Biotechnology Advances, 23: 41-61.*
Li et al., 1999, FEBS Letters, 456 :13-15.*
Sirko, A. et al., "Sulfate and Thiosulfate Transport in *Escherichia coli* K-12: Nucleotide Sequence and Expression of the cysTWAM Gene Cluster," Journal of Bacteriology, vol. 172, No. 6, Jun. 1990, pp. 3351-357, XP008042789.
Salcedo, E. et al., "A Glycine-Cleavage Complex as Part of the Folate One-Carbon Metabolism of *Plasmodium falciparum*," TRENDS in Parasitology, Sep. 2005, vol. 21, No. 9, pp. 1-7.

* cited by examiner

*Primary Examiner* — Anne-Marie Falk
(74) *Attorney, Agent, or Firm* — DLA Piper LLP (US)

(57) ABSTRACT

A method of producing methionine, derivatives or precursors thereof comprising culturing a microorganism modified to enhance production of cysteine in a culture medium comprising a source of carbon and a source of sulfur and recovering methionine from the culture medium. A microorganism for fermentative production of methionine or its derivatives in which production of methionine or derivatives thereof, wherein the microorganism enhances production of cysteine.

12 Claims, No Drawings

SEQUENCE LISTING

<160> NUMBER OF SEQ ID NOS: 20

<210> SEQ ID NO 1
<211> LENGTH: 127
<212> TYPE: DNA
<213> ORGANISM: Artificial
<220> FEATURE:
<223> OTHER INFORMATION: Synthetic Oligonucleotide

<400> SEQUENCE: 1

```
gccaggctct gattcagggc atcccgctgg ctggcgtgaa aaaagctcat aatatacctc      60
cttattccac acattatacg agccggatga ttaattgtca acagctctgt aggctggagc     120
tgcttcg                                                                127
```

<210> SEQ ID NO 2
<211> LENGTH: 136
<212> TYPE: DNA
<213> ORGANISM: Artificial
<220> FEATURE:
<223> OTHER INFORMATION: Synthetic Oligonucleotide

<400> SEQUENCE: 2

```
ccttcatctt tacatctgga cgtctaaacg gatagatgtg cacaacacaa catataacta      60
caagcgattg atgaggtaag gttcacactg gctcaccttc gggtgggcct ttctgccata     120
tgaatatcct ccttag                                                      136
```

<210> SEQ ID NO 3
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 3

```
gcccggtact catgttttcg ggtttatgg                                         29
```

<210> SEQ ID NO 4
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 4

```
ccgttattcc agtagtcgcg tgcaatgg                                          28
```

<210> SEQ ID NO 5
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 5

```
ttatcatgag agtgttgaag ttcggcggta catcagtggc                             40
```

<210> SEQ ID NO 6
<211> LENGTH: 39
<212> TYPE: DNA
<213> ORGANISM: Artificial
<220> FEATURE:
<223> OTHER INFORMATION: Synthetic Oligonucleotide

<400> SEQUENCE: 6
ttacccgggc cgccgccccg agcacatcaa acccgacgc                              39

<210> SEQ ID NO 7
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 7
ccgacagtaa gacgggtaag cctg                                              24

<210> SEQ ID NO 8
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 8
agcttagtaa agccctcgct ag                                                22

<210> SEQ ID NO 9
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 9
ccaatctgaa taacatggca atgtccagcg tttctggccc ggg                         43

<210> SEQ ID NO 10
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 10
cccgggccag aaacgctgga cattgccatg ttattcagat tgg                         43

<210> SEQ ID NO 11
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 11
ggagggacag ctgatacgaa agaagtccgc gaactggcgc                             40

<210> SEQ ID NO 12
<211> LENGTH: 47
<212> TYPE: DNA
<213> ORGANISM: Artificial
<220> FEATURE:
<223> OTHER INFORMATION: Synthetic Oligonucleotide

<400> SEQUENCE: 12
atacgcagct gggacattag atcccatccc catactcaaa tgtatgg                     47

```
<210> SEQ ID NO 13
<211> LENGTH: 140
<212> TYPE: DNA
<213> ORGANISM: Artificial
<220> FEATURE:
<223> OTHER INFORMATION: Synthetic Oligonucleotide

<400> SEQUENCE: 13
gcaccagaat acgttcattt aactgcgcac gcagttgttc cactttgctg ctcatgtctg      60
tcctccagta catgcaaccc cacacattat acgagccgga tgattaattg tcaacagctc     120
tgtaggctgg agctgcttcg                                                 140

<210> SEQ ID NO 14
<211> LENGTH: 100
<212> TYPE: DNA
<213> ORGANISM: Artificial
<220> FEATURE:
<223> OTHER INFORMATION: Synthetic Oligonucleotide

<400> SEQUENCE: 14
gcttttacca cagatgcgtt tatgccagta tggtttgttg aatttttatt aaatctgggt      60
tgagcgtgtc gggagcaagt catatgaata tcctccttag                           100

<210> SEQ ID NO 15
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 15
cctttgaggt cgcatggcca gtcggc                                           26

<210> SEQ ID NO 16
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 16 gcttttaat agaggcgtcg ccagctcctt gcc                                    33

<210> SEQ ID NO 17
<211> LENGTH: 130
<212> TYPE: DNA
<213> ORGANISM: Artificial
<220> FEATURE:
<223> OTHER INFORMATION: Synthetic Oligonucleotide

<400> SEQUENCE: 17
gcctgatgcg acgcttgcgc gtcttatcag gtctacaggt tacaaacctt gccataatat      60
acctccttac cacacattat acgagccgga tgattaattg tcaacagctc catatgaata    120
tcctccttag                                                           130

<210> SEQ ID NO 18
<211> LENGTH: 107
<212> TYPE: DNA
<213> ORGANISM: Artificial
<220> FEATURE:
<223> OTHER INFORMATION: Synthetic Oligonucleotide
```

```
<400> SEQUENCE: 18
ggttgagtga atgttaaacg cccggaggcg cttcccgcga tccgggcttt ttatcacact        60
ggctcacctt cgggtgggcc tttctgctgt aggctggagc tgcttcg                    107

<210> SEQ ID NO 19
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 19
ggtgacaaga atcagttccg c                                                 21

<210> SEQ ID NO 20
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 20
gcgtttattc gttggtctgc                                                   20
```

METHODS FOR PRODUCING METHIONINE BY CULTURING A MICROORGANISM MODIFIED TO ENHANCE PRODUCTION OF CYSTEINE

RELATED APPLICATIONS

This is a §371 of International Application No. PCT/EP2006/050033, with an international filing date of Jan. 4, 2006 (WO 2007/07041 A1, published Jul. 12, 2007).

TECHNICAL FIELD

This disclosure relates to processes for the production of methionine or its derivatives by culturing a microorganism in an appropriate culture medium comprising a source of carbon and a source of sulfur. The microorganism is modified in a way that the production of cysteine and/or C1 units is enhanced an or the transfer potential of the C1 units on homocysteine is increased or optimized. The isolation of methionine or its derivates from the fermentation medium is also claimed.

BACKGROUND

Sulfur-containing compounds such as cysteine, homocysteine, methionine or S-adenosylmethionine are critical to cellular metabolism, and are produced industrially to be, used as food or feed additives and pharmaceuticals. In particular methionine, an essential amino acid, which cannot be synthesized by animals, plays an important role in many body functions. Aside from its role in protein biosynthesis methionine is involved in transmethylation and in the bioavailability of selenium and zinc. Methionine is also directly used as a treatment for disorders like allergy and rheumatic fever. Nevertheless most of the methionine which is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunderson, C. L., (1985) British Journal of Nutrition 54, 621633). Pure L-methionine can be produced from racemic methionine e.g. through the acylase treatment of N-acetyl-D,L-methionine which increases production costs dramatically. The increasing demand for pure L-methionine coupled to environmental concerns render microbial production of methionine attractive.

Microorganisms have developed highly complex regulatory mechanisms that fine-tune the biosynthesis of cell components thus permitting maximum growth rates. Consequently only the required amounts of metabolites, such as amino acids, are synthesized and can usually not be detected in the culture supernatant of wild-type strains. Bacteria control amino acid biosynthesis mainly by feedback inhibition of enzymes, and repression or activation of gene transcription. Effectors for these regulatory pathways are in most cases the end products of the relevant pathways. Consequently, strategies for overproducing amino acids in microorganisms require the deregulation of these control mechanisms.

The pathway for L-methionine synthesis is well known in many microorganisms. Methionine is derived from the amino acid aspartate, but its synthesis requires the convergence of two additional pathways, cysteine biosynthesis and C1 metabolism (N-methyltetrahydrofolate). Aspartate is converted into homoserine by a sequence of three reactions. Homoserine can subsequently enter the threonine/isoleucine or methionine biosynthetic pathway. In *E. coli* entry into the methionine pathway requires the acylation of homoserine to succinyl-homoserine. This activation step allows subsequent condensation with cysteine, leading to the thioether-containing cystathionine, which is hydrolyzed to give homocysteine. The final methyl transfer leading to methionine is carried out by either a $B_{12}$-dependent or a $B_{12}$-independent methyltransferase. Methionine biosynthesis in *E. coli* is regulated by repression and activation of methionine biosynthetic genes via the MetJ and MetR proteins, respectively (reviewed in Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds), 1996, *Escherichia coil* and *Salmonella*: Cellular and Molecular Biology. American Society for Microbiology, Weissbach et al., 1991 Mol. Microbiol., 5, 1593-1597). MetJ together with its corepressor S-adenosylmethionine is known to regulate the genes metA, metB, et metE and metF. Other genes encoding enzymes implicated in methionine production, such as glyA, metE, metH and metF are activated by MetR whereas metA is repressed by MetR. The corresponding enzymes are all involved in the production and the transfer of C1 units from serine to methionine. GlyA encoding serine hydroxymethyltransferase catalyzes the conversion of serine to glycine and the concomitant transfer of a C1 unit on the coenzyme tetrahydrofolate (THF). The C1 unit in form of methylene-THF needs to be reduced to methyl-TH before it can be transferred on homocysteine to yield methionine. This reaction is catalyzed by the MetF protein. Transfer of the methylgroup is either catalyzed by MetH via vitamin B12 or directly by MetE. The MetH enzyme is known to have a catalytic rate that is hundred times higher than the MetE enzyme. In the absence of vitamin B12 and thus active MetH Me E can compose up to 5% of the total cellular protein. The presence of active MetH reduces MetE activity probably by reducing the amount of homocysteine that normally activates the transcription of metE via MetR. Therefore the production of methionine via MetH save important resources for the cell by not expressing large quantities of MetE. An accumulation of homocysteine is toxic for *E. coli* (Tuite; et al., 2005 J. Bacteriol, 187, 13, 4362-4371.) and at the same time has a negative, regulatory effect on metA expression via MetR. Thus strong expression of the enzymes MetH and/or MetE is clearly required for efficient methionine production.

In *E. coli* reduced sulfur is integrated into cysteine and then transferred onto the methionine precursor O-succinyl-homoserine, a process called transulfuration (reviewed in Neidhardt, F. C. (Ed. in Chief), W Curtiss III, J. L. Ingraham, E. C. C. Lin, K. B. Low, B. Magasanik, W. S. Reznikbff, M. Riley, M. Schaechter and H. E. Umbarger (eds). 1996. *Escherichia coli* and *Salmonella*: Cellular and Molecular Biology. American Society for Microbiology). Cysteine is produced from O-acetylserine and $H_2S$ by sulfhydrylation. The process is negatively feed-back regulated by the product, cysteine, acting on serine transacetylase, encoded by CysE. N-acetyl-serine, which is spontaneously produced from O-acetyl-serine, together with the transcription factor CysB activates genes encoding enzymes involved in the transport of sulfur compounds, their reduction to H2S and their integration in the organo-sulfur compound cysteine, which as methionine is an essential amino acid.

In the absence of cysteine, MetB catalyzes the conversion of the methionine-precursor O-succinyl homoserine into ammonia, α-ketobutyrate and succinate, a reaction called γ-elimination (Aitken & Kirsch, 2005, Arch Biochem Biophys. 433, 166-75). α-ketobutyrate can subsequently be converted into isoleucine. This side reaction is not desirable for the industrial production of methionine, since the two amino acids are difficult to separate. Thus low γ-elimination activity is an important aspect for the industrial production of methionine. The provisional patent application U.S. 60/650, 124 filed on Feb. 7, 2005 describes how γ-elimination can be reduced by optimizing the enzyme MetB. Optimizing the flow of cysteine biosynthesis can also reduce γ-elimination and thus the production of the byproduct isoleucine and constitutes an embodiment of this invention.

SUMMARY

We provide processes for producing methionine, its precursors or products derived thereof in a fermentative process using microorganisms that have an increased production of cysteine and that grow on a defined carbon and sulfur source.

Precursors of methionine are defined as metabolites that are part of the methionine specific metabolic pathway or can be derived of these metabolites. The methionine specific pathway starts with the transformation of homoserine to succinyl-homoserine by the enzyme homoserine, succinyl transferase (MetA).

Products derived of methionine originate from methionine transforming and/or, degrading pathways.

To increase cysteine production we enhanced the expression of genes involved in cysteine production.

The term "enhanced" in this context describes the increase in the intracellular activity of an enzymatic activity which is encoded by the corresponding DNA, for example, by increasing the number of copies of the gene, using a strong promoter or using an allele with increased activity and possibly combining these measures.

The terms "increased expression" or "enhanced expression" are both used, in the text and have similar meaning.

To increase the expression of a gene it may be encoded chromosomally or extrachromosomally. Chromosomally there may be one z r several copies on, the genome that can be introduced by known methods of recombination. Extrachromosomally genes may be carried by different types of plasmids that differ with respect to their origin of replication and thus their copy number in the cell. They may be present as 1-5 copies, ca 20 or up to 500 copies, corresponding to low copy number plasmids with tight replication (pSC011, RK2), low copy number plasmids (pACYC, pRSF1010) or high copy number plasmids (pSK bluescript II).

The gene may be expressed using promoters with different strength that need or need not to be induced by inducer molecules. These promoters may be homologous or heterologous. Examples are the promoters Ptrc, Ptac, Plc, the lambda promoter cl or other promoters known to the expert in the field.

Expression of the target genes may be boosted or reduced by elements stabilizing or destabilizing the corresponding messenger RNA (Carrier and Keasling (1998) Biotechnol. Prog. 15, 58-64) or the protein (e.g. GST tags, Amersham Biosciences).

We also provide microorganisms that contain one or several alleles of the gene to be enhanced.

The expression of genes involved in cysteine production may be enhanced.

Genes involved in cysteine production comprise genes encoding proteins required for the import of a sulfur source, the transformation of that sulfur source into hydrogen sulfide and the assimilation of hydrogen sulfide or the sulfur source into cysteine or its derivatives.

In *E. coli* these proteins are encoded by the followings genes (followed by accession numbers and function of the corresponding polypeptide):

| gene | accession number | function |
|---|---|---|
| cysA | 1788761 | sulfate permease |
| cysU, cysT | 1788764 | component of sulfate ABC transporter |
| cysW | 1788762 | membrane bound sulfate transport protein |
| cysZ | 1788753 | ORF upstream of cysK |
| cysN | 1789108 | ATP sulfurylase |
| cysD | 1789109 | sulfate adenylyltransferase |
| cysC | 1789107 | adenylylsulfate kinase |
| cysH | 1789121 | adenylylsulfate reductase |
| cysI | 1789122 | sulfite reductase, alpha subunit |
| cysJ | 1789123 | sulfite reductase, beta subunit |
| cysE | 1790035 | serine acetyltransferase |
| cysK | 1788754 | cysteine synthase |
| cysM | 2367138 | O-acetyl serine sulfhydrylase |
| cysZ | 1788753 | sulfate transport |
| sbp | 1790351 | Periplasmic sulfate-binding protein |

Genes and proteins may be identified using the denominations of the corresponding genes in *E. coli*. However, and unless specified otherwise, use of these denominations has a more general meaning and covers all the corresponding genes and proteins in other organisms, more particularly microorganisms. PFAM (protein families database of alignments and hidden Markov models; http://www.sanger.ac.uk/Software/Pfam/) represents a large collection of protein sequence alignments. Each PFAM makes it possible to visualize multiple alignments, see protein domains, evaluate distribution among organisms, gain access to other databases, and visualize-known protein structures.

COGs (clusters of orthologous groups of proteins, http://www.ncbi.nlm.nih.gov/COG/) are obtained by comparing protein sequences from 66 fully sequenced genomes representing-30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website, http://www.ncbi.nlm.nih.gov/BLAST/ with the default parameters indicated on that website. The sequences obtained can then be exploited (e.g., aligned) using, for example, the programs CLUSTAL. (http://www.ebi.ac.uk/clustalw/) or MULTALIN (http://prodes.toulouse.inra.fr/multalin/cgi-bin/multalin.pl), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, N.Y.).

The microorganism may be modified to increase the expression of cysE encoding serine transacetylase.

We also provide microorganisms that contain one or several alleles encoding serine transacetylase.

Such strains are characterized by the fact that they possess a cysteine metabolism which permits an increased flux towards methionine by providing an increased substrate concentration for the synthesis of γ-cystathionine, a reaction catalyzed by MetB. At low cysteine concentrations the MetB enzyme produces ammonia, succinate and α-ketobutyrate from succinyl-homoserine, a reaction called γ-elimination. An increased cysteine concentration reduces the amount of α-ketobutyrate produced and thus increases the flow towards methionine.

Enhanced expression of serine transacetylase activities can be validated in enzymatic tests with serine and acetyl-CoA. The react on is started by adding the protein extract containing serine transacetylase activity, and the formation of O-acetyl-serine, is monitored by GC-MS after protein precipitation and derivatization with a silylating reagent.

We also provide for enhanced expression of the cysM gene encoding O-acetylserine sulfhydrylase which allows increased integration of thiosulfate into sulfocysteine boosting the production of cysteine.

We thus disclose processes in which γ-elimination and thus the production of isoleucine is reduced by optimizing the production of cysteine.

A heterologous promoter is understood as the modified wildtype promoter or any promoter from another organism or an entirely synthetic promoter. Preferentially the heterologous promoter is a strong promoter, such as Ptrc, Ptac, lamda cI or other known promoters.

We further provide processes in which a microorganism is used for the production of methionine or its derivatives in which the expression of genes involved in the production of C1 units and/or their transfer potential onto homocysteine is/are increased.

Increases are accomplished by adapting the expression level of the concerned gene in a way to obtain the highest methionine production. In most cases this is done by creating expression libraries of the concerned gene using for example heterologous promoters and screening for the best producers.

The term "C1 unit-" describes single carbon atoms that are bound to the carrier molecule tetrahydrofolate as methyl, methylene, methenyl or formyl groups.

The term "transfer potential" describes the capability of the microorganisms to transfer C1 units onto homocysteine. This potential is determined by the activities of MetF and/or MetH that have been enhanced and/or optimized by the inventors.

Genes involved in the production of C1 units are listed below:

| | | |
|---|---|---|
| serA | 1789279 | phosphoglycerate dehydrogenase |
| serB | 1790849 | phosphoserine phosphatase |
| serC | 1787136 | phosphoserine aminotransferase |
| glyA | 1788902 | serine hydroxymethyltransferase |
| gcvT | 1789272 | Tetrahydrofolate dependent aminomethyl transferase |
| gcvH | 1789271 | Glycine cleavage, carrier of aminomethyl group |
| gcvP | 1789269 | Glycine dehydrogenase (decarboxylating) |
| lpd | 1786307 | Lipoamide dehydrogenase |

Genes involved in the transfer of C1 units onto homocysteine are listed below:

| | | |
|---|---|---|
| metF | 1790377 | 5,10-Methylenetetrahydrofolate reductase |
| metH | 1790450 | B12-dependent homocysteine-N5-methyltetrahydrofolate transmethylase |
| metE | 2367304 | Tetrahydropteroyltriglutamate methyltransferase |

The microorganism may be used for the production of methionine is modified to increase expression of metF or metH, or both or to express metF from a heterologous promoter.

Enhanced vitamin B12 dependent methionine synthase (MetH) activity can be validated in enzymatic tests with methyl-THF and homocysteine in the presence of vitamin B12 and SAM. The reaction is started by adding the protein extract containing the methylene tetrahydrofolate reductase activity, and the formation of methionine is monitored by GC-MS after protein precipitation and derivatization with a silylating reagent.

Methionine production can be further increased by increasing the expression of additional genes involved in methionine biosynthesis, which is also object of the invention.

Selected genes are listed below:

| | | |
|---|---|---|
| metA | 1790443 | Homoserine succinyltransferase |
| metB | 1790375 | Cystathionine-γ-synthase |
| metC | 1789383 | Cystathionine-β-lyase |
| metF | 1790377 | 5,10-Methylenetetrahydrofolate reductase |
| metR | 1790262 | Positive regulatory gene for metE, metH and metF |

Furthermore, expression of genes in pathways degrading methionine or deviating from the methionine production pathway may be reduced or the genes may be deleted.

| | | |
|---|---|---|
| speD | 1786311 | S-Adenosylmethionine decarboxylase |
| speC | 1789337 | Ornithine decarboxylase |
| astA | 1788043 | Arginine succinyltransferase |
| dapA | 1788823 | Dihydrodipicolinate synthase |

Anaplerotic reactions may be boosted by expressing

| | | |
|---|---|---|
| ppc | 1790393 | phosphoenolpyruvate carboxylase |
| pps | 1787994 | phosphoenolpyruvate synthase |

Acetate consuming reactions may be booster by over-expressing

| | | |
|---|---|---|
| acs | 1790505 | acetyl-CoA synthetase |

An additional increase in the production of L-methionine, its precursors or compounds derived thereof can be achieved by overexpressing one or several of the following genes: pyruvate cartboxylases, e.g. from *Rhizobium etli* (pyc, U51439), or one of its homologs, the homoserine synthesizing enzymes encoded by the genes thrA (homoserine dehydrogenase/aspartokinase, 1786183), preferably with reduced feed-back sensitivity, metL (homoserine dehydrogenase/aspartokinase, g1790376) or lysC (aspartokinase, 1790455) and asd (aspartate semialdehyde dehydrogenase).

A further increase in the production of L-methionine, its precursors or compounds derived thereof, is achieved by means of deleting the gene for the repressor protein MetJ, responsible for the down-regulation of the methionine regulon as was suggested in JP 2000157267-A/3 (see also GenBank 1790373).

Methionine production is further increased by using homoserine succinyltransferase alleles with reduced feedback sensitivity to its inhibitors SAM and methionine as described in WO 2005/111202 that is incorporated herein by reference in its entirety.

An increase in the production of L-methionine its precursors or compounds derived thereof, can be achieved by attenuating the activity or deleting one of the following genes.

Attenuation in this context describes the red action of the intracellular activity of an enzyme by measures such as reducing its expression, reducing the stability of the enzyme, increasing its degradation and/or other known solutions.

| Gene | Genbank entry | activity |
|---|---|---|
| ackA | 1788633 | acetate kinase |
| pta | 1788635 | phosphotransacetylase |
| aceE | 1786304 | pyruvate deydrogenase E1 |
| aceF | 1786305 | pyruvate deydrogenase E2 |
| lpd | 1786307 | pyruvate deydrogenase E3 |
| sucC | 1786948 | succinyl-CoA synthetase, beta subunit |
| sucD | 1786949 | succinyl-CoA synthetase, alpha subunit |
| pck | 1789807 | phosphoenolpyruvate carboxykinase |
| pykA | 1788160 | pyruvate kinase II |
| pykF | 1787965 | pyruvate kinase I |
| poxB | 1787096 | pyruvate oxidase |
| ilvB | 1790104 | acetphydroxy acid synthase I, large subunit |
| ilvN | 1790103 | acetohydroxy acid synthase I, small subunit |
| ilvG | 1790202 1790203 | acetohydroxy acid synthase II, large subunit |
| ilvM | 1790204 | acetohydroxy acid synthase II, small subunit |
| ilvI | 1786265 | acetohydroxy acid synthase III, large subunit |
| ilvH | 1786266 | acetohydroxy acid synthase III, small subunit |
| aroF | 1788953 | DAHP synthetase |
| aroG | 1786969 | DAHP synthetase |
| aroH | 1787996 | DAHP synthetase |
| thrB | 1786184 | homoserine kinase |
| thrC | 1786185 | threonine synthase |
| sdaA | 1788116 | serine deaminase |
| sdaB | 1789161 | serine deaminase |

Production of methionine may be further increased by using an altered metB allele that uses preferentially or exclusively $H_2S$ and thus produces homocysteine from O-succinyl-homoserine as has been described in WO 2004/076659, the contents of which are incorporated herein by reference.

The sulfur source used for the fermentative production of L-methionine, its precursors or compounds derived thereof, may be an of the following or a combination thereof: sulfate, thiosulfate, hydrogen sulfide, dithionate dithionite sulfite.

The sulfur source may be sulfate and/or thiosulfate.

We also provide the process, for the production of L-methionine, its precursors or compounds derived thereof, comprising the fermentation of the methionine producing microorganism; described above, the concentration of methionine, its precursors or derivatives and the isolations of the desired product of the fermentation n broth.

The terms 'culture' and 'fermentation' are used indifferently to denote the growth of a microorganism on an appropriate culture-medium containing a simple carbon source.

A simple carbon source is a source of carbon that can be used by those skilled in the art to obtain normal growth of a microorganism, in particular of a bacterium. In particular it can be an assimilable sugar such as glucose, galactose, sucrose, lactose or molasses, or by-products of these sugars. An especially preferred simple carbon source is glucose. Another preferred simple carbon source is sucrose.

Those skilled in the art are able to define the culture conditions for the microorganisms. In particular the bacteria may be fermented at a temperature between 20° C. and 55° C., preferentially between 25° C. and 40° C., and more specifically about 30° C. for *C. gluiamicum* and about 37° C. for *E. coli*.

The fermentation is generally conducted it fermenters with an inorganic culture medium of known defined composition adapted to the bacteria used, containing at least one simple carbon source, and if necessary a co-substrate necessary or the production of the metabolite.

In particular; the inorganic culture medium for *E. coli* can be of identical or similar composition to an M9 medium (Anderson, 194, *Proc. Natl. Acad. Sci. USA* 32:120-128), an M63 medium (Miller, 1992, A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

Analogously the inorganic culture medium for *C. glutamicum* can be of identical or similar composition to BMCG medium (Liebl et al, 1989, *Appl. Microbiol. Biotechnol.* 32: 205-210) or to a medium such as that described by Riedel et al. (2001, *J. Mol. Microbiol. Biotechnol.* 3: 573-583). The media can be supplemented to compensate, for auxotropbies introduced by mutations.

After fermentation L-methionine, its precursors or compounds derived thereof, is/are recovered and purified if necessary. The method for the recovery and purification of the produced compound such as methionine in the culture media are well known to those skilled in the art.

Optionally from 0 to 100% of the biomass may be retained during the purification of the fermentation product.

We also provide microorganisms that increase fermentative production of methionine.

The term "optimized microorganism." describes the microorganism into which the above described modifications are integrated leading to the best industrial performance for the production of the desired metabolite(s) and possibly the lowest production of sideproducts.

In a preferred application the organism is either *E. coli* or *C. glutamicum* or *Saccharomyces cerevisiae*.

In the most preferred application the organisms is *E. coli*.

DETAILED DESCRIPTION

An *E. coli* strain in which the methionine repressor encoded by the metJ gene has been replaced by a chloramphenicol cassette (ΔmetJ::Cm) and that harbors a metA allele with reduced feed-back sensitivity to methionine and SAM (metA*11) has been described in PCT No PCT/IB04/001901 filed on May 12, 2004, the subject matter of which is incorporated herein by reference. Into this strain the following genetic modifications were introduced.

Construction of MG1655 metA*11 ΔmetJ::Cm Ptrc-metF:: Km

To clone the metF gene under the control of the heterologous Ptrc promoter, the homologous recombination strategy described by Datsenko & Wanner (2000) was used. This strategy allows the insertion of a chloramphenicol or a kanamycin resistance cassette near the genes concerned. For this purpose the following oligonucleotides were used:

PtrcmetF R (SEQ ID NO 1)
GCCAGGCTCTGATTCAGGGCATCCCGCTGGCTGGCGTGAAAAAAGCTCAT aatatacctccttattccacac *attata*cgagccggatgattaat

*tgtcaa*cagct cTGTAGGCTGGAGCTGCTTCG with:
    a region (upper case) homologous to the sequence (4130259-4160195) of the gene, metF (reference sequence on the website http://genolist.pasteur.fr/Colibri/)

a region (italic case) homologous to the promoter Ptrc sequence with the RBS (bold) the −35 and −10 boxes (bold)

a region (upper case) for the amplification of the kanamycin resistance cassette (reference sequence in Datsenko, K. A. & Wanner, B. L., 2000, PNAS, 97: 6640-6645)

```
Ptrc-metF F
                                              (SEQ ID NO 2)
ccttcatctttacatctggacgtctaaacggatagatgtgcacaacaa catataactacaagcgattgatgaggtaaggt tcacactggctcaccttcg ggtgggcctttctgcCATATGAATATCCTCCTTAG
``` with:
- a region (lower case) homologous to the sequence (4130114-4130195) of the region of gene metF (reference sequence on the web site http)://genolist.pasteur.fr/Colibri/)
- a region (italics, lower case) homologous to the sequence of the bacteriophage T7 terminus (Genbank V01146)
- a region (upper case) for the amplification of the kanamycin resistance cassette (reference sequence in Datsenko, K. A. &. Wanner, B. L. 2000, PNAS, 97: 6640-6645).

The oligonucleotides Ptrc-metF F and Ptr-metF R were used to amplify the kanamycin resistance cassette from the plasmid pKD4. The PCR product obtained was then introduced by electroporation into the strain MG1655 metA*11 ΔmetJ (pKD46), in which the Red recombinase enzyme expressed permits the homologous recombination. The kanamycin resistant transformants were selected and the insertion of the resistance cassette was verified by a PCR analysis with the oligonucleotides Ptrc-metFv F and Ptrc-metFv R defined below.

```
Ptrc-metFv F (SEQ ID NO 3):
GCCCGGTACTCATGTTTTCGGGTTTATGG (homologous to the
sequence from 4129866 to 4129894).

Ptrc-metFv R (SEQ ID NO 4):
CCGTTATTCCAGTAGTCGCGTGCAATGG (homologous to the
sequence from 4130524 to 4130497).
```

The resulting strain was called MG1655 metA*11 ΔmetJ Ptrc-metF::Km.

Construction of plasmid pME101-thrA*1-cysE
pME101-thrA*1

To boost the production of homoserine thrA* encoding aspartokinase/homoserine with reduced feed-back resistance to threonine, was expressed from the plasmid pCL1920 (Lerner & Inouye, 1990, NAR 18, 15 p 4631 using the promoter Ptrc. For the construction of the plasmid pME101-thrA.*1 thrA was PCR amplified from genomic DNA using; the following oligonucleotides:

```
BspH1thrA (SEQ ID NO 5):
ttaTCATGAgagtgttgaagttcggcggtacatcagtggc

SmaIthrA (SEQ ID NO 6):
ttaCCCGGGccgccgcccgagcacatcaaacccgacgc
```

The PCR amplified fragment was cut with the restriction enzymes BspHI and SmaI and cloned into the NcoI/SmaI sites of the vector pTRC99A (Stratagene). For the expression from a low copy vector the plasmid pME011 was constructed as follows. The plasmid pCL1920 was PCR amplified using the oligonucleotides PME101F and PME101R and the BstZ171-XmnI fragment from the vector pTRC99A harboring the lacI gene and the Ptrc promoter were inserted into the amplified vector. The resulting vector and the vector harboring the thrA gene were restricted by ApaI and SmaI Land the thrA containing fragment was cloned into the vector PME101. To relieve ThrA from feed-back inhibition the mutation F318S was introduced by site-directed mutagenesis (Stratagene) using the oligonucleotides ThrAF F318S and ThrAR F318S, resulting in the vector pME101-thrA*1.

```
PME101F (SEQ ID NO 7):
Ccgacagtaagacgggtaagcctg

PME101R (SEQ ID NO 8):
Agcttagtaaagccctcgctag

ThrAF F318S (SmaI) (SEQ ID NO 9):
Ccaatctgaataacatggcaatgtccagcgtttctggcccggg

ThrAR F318S (SmaI) (SEQ ID NO 10):
Cccgggccagaaacgctggacattgccatgttattcagattgg
``` pME101-thrA*1-cysE

For the construction of pME101-thrA*1-cysE the cysE gene was amplified by PCR using oligonucleotides Ome. B001 and Ome B002, the PCR-product was cut with the restriction enzyme PvuII and cloned into the SmaI site of the vector pME101-thrA*1 resulting in the vector pME101-thrA1-cysE.

```
Ome B001_cysER-PvuII
                                             (SEQ ID NO 11)
GGAGGGACAGCTGATACGAAAGAAGTCCGCGAACTGGCGC Ome B002_cysEF-PvuII
                                             (SEQ ID NO 12)
Atacgcagctgggacattagatcccatcccatactcaaatgtatgg
PvuII site are underlined.
The sequence in bold corresponds to cysE
(Colibri) (3780423-3780397)
```

Construction of MG1655 metA*11 ΔmetJ::Cm Ptrc-metH::Km

To boost the production of methionine the metH gene was overexpressed using the Ptrc promoter. For the construction the following oligonucleotides were used:

```
DiclR-metHF
                                             (SEQ ID NO 13)
gcaccagaatacgttcatttaactgcgcacgcagttgttccactttgctg ctcatGTCTGT CCTCCAGTACATGCAACCCCACAC ATTATACGAGCCGG

ATGATTAAT TGTCAACAGCTCTGTAGGCTGGAGCTGCTTCG
``` with:
- a region (lower case) homologous to the sequence (4221461-4221408) of the gene metH (reference sequence on the website http://genolist.pasteur.fr/Colibri/)
- a region (italics, upper case) homologous to the promoter Ptrc sequence with the RBS (bold) the −35 and −10 boxes (bold)
- a region (upper case) for the amplification 6 the kanamycin resistance cassette (reference sequence in Datsenko, K. A. & Wanner, B. L., 2000, PNAS, 97: 6640-6645).

```
iclR-metHF
                                             (SEQ ID NO 14)
GCTTTTACCACAGATGCGTTTATGCCAGTATGGTTTGTTGAATTTTTATT

AAATCTGGGTTGAGCGTGTCGGGAGCAAGTCATATGAATATCCTCCTTAG
``` with:
- a region (italics, upper case) homologous to the sequence (4221327-4221406) of the region of gene metH (reference sequence on the website http://genolist.pasteur.fr/Colibri/),
- a region (upper case) for the amplification of the kanamycin resistance cassette (reference sequence in Datsenko, K. A. & Wanner, B. L., 2000, PNAS, 97: 6640-6645).

The oligonucleotides DiclR-metHF and iclR-metHF were used to amplify the kanamycin resistance cassette from the plasmid pKD4. The PCR product obtained is then introduced by electroporation into the strain MG1655 metA*11 ΔmetJ (pKD46), in which the Red recombinase enzyme was expressed permitting the homologous recombination. Kanamycin resistant transformants are selected and the insertion of the resistance cassette was verified by a PCR analysis with the oligonucleotides iclF and iclR defined below.

```
iclF (SEQ ID NO 15):
CCTTTGAGGTCGCATGGCCAGTCGGC
(homologous to the sequence from 4221558 to
4221533).

iclR (SEQ ID NO 16):
GCTTTTTAATAGAGGCGTCGCCAGCTCCTTGCC
(homologous to the sequence from 4219917 to
4219949).
```

The resulting strain was called MG1655 metA*11 ΔmetJ Ptrc-metH:Km

Construction of MG1655 metA*11 ΔmetJ::Cm Ptrc-metF:Km Ptrc-metH

For the construction of the strain MG1655 metA*11ΔmetJ::Cm Ptrc-metF:Km Ptrc-metH the chloramphenicol and the kanamycin resistance cassette was eliminated from the strain MG1655 metA*11 ΔmetJ::Cm Ptrc-metH:Km.

The plasmid pCP20 carrying FLP recombinase acting at the FRT sites of the chloramphenicol resistance cassette was introduced into the recombinant strain by electroporation. After a series of cultures at 42° C., the loss of the two cassettes was verified by PCR analysis. The strain retained was designated MG1655 metA*11 ΔmetJ Ptrc-metH.

To transfer the promoter construct Ptrc-:metF: Km into the strain MG1655 metA*11 ΔmetJ Ptrc-metH, the method of phage P1 transduction was used. The protocol followed was implemented in 2 steps with the preparation of the phage lysate of the strain MG1655 MG1655 metA*11 ΔmetJ Ptrc-metF:Km and the subsequent transduction into strain MG1655 metA*11 ΔmetJ Ptrc-metH Preparation of Phage Lysate P1:
- Inoculation with 100 μl of an overnight culture of the strain MG1655 metA*11 ΔmetJ Ptrc-metF:Km of 10 ml of LB+Km 50 μg/ml+glucose 0.2%+CaCl$_2$ 5 mM.
- Incubation for 30 min at 37° C. with shaking.
- Addition of 100 μl of phage lysate P1 prepared on the strain MG1655 (about 1.10$^9$ phage/ml).
- Shaking at 37° C. for 3 hours until all cells were lysed.
- Addition of 200 μl chloroform and vortexing.
- Centrifugation for 10 min at 4500 g to eliminate cell debris.
- Transfer of the supernatant to a sterile tube and addition of 200 μl chloroform.
- Storage of lysate at 4° C.

Transduction
- Centrifugation for 10 min at 1500 g of 5 ml of an overnight culture of the strain MG1655 metA*11 ΔmetJ Ptrc-metH in LB medium.
- Suspension of the cell pellet in 2.5 ml of 10 mM MgSO$_4$, 5 mM CaCl$_2$
- Control tubes: 100 μL cells
  100 μl phages P1 of strain MG1655 metA*11 ΔmetJ Ptrc-metF:Km
- Test tube: 100 μl of cells+100 μl of phages P1 of the strain MG1655 metA*11 ΔmetJ Ptrc-metF:Km
- Incubation for 30 min at 30° C. without shaking.
- Addition of 100 μl of 1 M sodium citrate in each tube and vortexing.
- Addition of 1 ml of LB.
- Incubation for 1 hour at 37° C. with shaking.
- Spreading-on dishes LB+Km 50 μg/ml after centrifuging of tubes for 3 min at 7000 rpm.
- Incubation at 37° C. overnight.

Verification of the Strain

Kanamycin resistant transformants were selected and the presence of the promoter construct Ptrc-metF:Km was verified by PCR analysis with the oligonucleotides Ptrc-metFv F and Ptrc-metFv R, described above. The strain retain d was designated MG1655 metA*11 ΔmetJ::Cm Ptrc-metH Ptrc-metF:Km.

Construction of MG1655 metA*11 ΔmetJ::Cm Ptrc-cysM::Km

To clone the cysM gene under the control of the heterologous Ptrc promoter, the homologous recombination strategy described by Datsenko & Wanner (2000) was used. This strategy allows the insertion of a chloramphenicol or a kanamycin resistance cassette near the genes concerned. For this purposes the following oligonucleotides were used:

```
Ptrc-cysM F
                                           (SEQ ID NO 17)
gcctgatgcgacgcttgcgcgtcttatcaggtctacaggttacaaaccttt gccataatatacctccttaccacac attatacgagccggatgattaat tgtcaacagctcCATATGAATATCCTCCTTAG
``` with:
- a region (lower case) homologous to the sequence (2537627-2537681) of the gene cysM (reference sequence on the website http)://genolist.pasteur.fr/Colibri/)
- a region (italics, lower case) homologous to the promoter Ptrc sequence with the RBS (bold) the −35 and −10 boxes (bold)
- a region (upper case) for the amplification of the kanamycin resistance cassette (reference sequence in Datsenko, K. A. & Wanner, B. L., 2000, PNAS, 97: 6640-6645),

```
Ptrc-cysM R
                                           (SEQ ID NO 18)
ggttgagtgaatgttaaacgcccggaggcgcttcccgcgatccgggcttt tTATCACACTGGCTCACCTTCGGGTGGGCCTTTCTGCTGTAGGCTGGAGC

TGCTTCG
``` with:
- a region (lower case) homologous to the sequence (2537734-2537684) of the region of gene cysM (reference sequence on the website http://genolist.pasteur.fr/Colibri)
- a region (italics, upper case) homologous to the sequence of the bacteriophage. T7 terminus (Genbank V01146)
- a region (upper case) for the amplification of the kanamycin resistance cassette (reference sequence in Datsenko, K. A. & Wanner, B. L., 2000, PNAS, 97: 6640-6645).

The oligonucleotides Ptrc-cysM F and Ptrc cysM R were used to amplify the kanamycin resistance cassette from the plasmid pKD4. The PCR product obtained was then introduced by electroporation into the strain MG1655 metA*11 ΔmetJ (pKD46), in which the Red recombinase enzyme was expressed permitting homologous recombination. Kanamycin resistant transformants were then selected and the insertion of the resistance cassette was verified by PCR analysis with the oligonucleotides Ptrc-cysMv F and Ptrc-cysMv R defined below.

```
Ptrc-cysMv F:
                                          (SEQ ID NO 19)
ggtgacaagaatcagttccgc
(homologous to the sequence from 2537262 to
2537282).

Ptrc-cysMv R:
                                          (SEQ ID NO 20)
GCGTTTATTCGTTGGTCTGC
(homologous to the sequence from 2537833 to
2537814).
```

The resulting strain is called MG1655 metA*11 ΔmetJ Ptrc-cysM::Km.

Construction of MG1655 metA*11 ΔmetJ Ptrc-metF Ptrc-metH Ptrc-cysM:Km

For the construction of the strain MG1655 metA*11ΔmetJ Ptrc-metF Ptrc-metH Ptrc-cysM:Km the chloramphenicol and kanamycin resistance cassettes were eliminated from the strain MG1655 metA*11 ΔmetJ:Cm Ptrc-metF:Km Ptrc-metH using plasmid pCP20, as described above. The strain retained was designated MG1655 metA*11 ΔmetJ Ptrc-metF Ptrc-metH To transfer the promoter construct Ptrc-cysM: Km into the strain MG1655 metA*11 ΔmetJ Ptrc-metF Ptrc-metH the method of phage P1 transduction was used. The protocol followed was implemented in 2 steps with the preparation of the phage lysate of the strain MG1655 MG1655 metA*11 ΔmetJ Ptrc-cysM:Km and the subsequent transduction into strain MG1655 metA*11 ΔmetJ Ptrc-metF Ptrc-metH as described above. The strain retained was designated MG1655 metA*11 ΔmetJ Ptrc-metF Ptrc metH Ptrc-cysM:Km.

Combining Enhanced Expression of CysE and MetH and Optimized Expression of metF and cysM with Alleles metA*11 and ΔmetJ For the construction of the strains MG1655 metA*11 ΔmetJ::Cm (pME101-thrA*1), MG1655 metA*11 ΔmetJ:: Cm Ptrc-metH:Km (pME111-thrA*1-cysE), MG1655 metA*11 ΔmetJ::Cm Ptrc-metH, Ptrc-metF:Km (pME101-thrA*1-cysE) and MG1655 metA*11 ΔmetJ Ptrc-metF Ptrc-metH Ptrc-cysM:Km (pME101-thrA*1-cysE) the plasmids (pME101-thrA*1) or (pME101-thrA*1-cysE) were introduced into the strains MG1655 metA*11 ΔmetJ::Cm, MG1655 metA*11 ΔmetJ::Cm Ptrc-metH:Km, MG1655 metA*11 ΔmetJ::Cm Ptrc-metH Ptrc-metF:Km and MG1655 metA*11 ΔmetJ Ptrc-metF Ptrc-metH Ptrc-cysM:Km by transformation.

Evaluation of Methionine Producing Strains with Enhanced Expression of cysE, metH and/or cysM and/or metF Under the Control of a Heterologous Promoter Production strains were initially evaluated in small Erlenmeyer flasks. A preculture was grown in LB medium with 2.5 g/l glucose and used to inoculate an overnight culture in minimal medium PC1. This culture serve to inoculate a 50 ml culture to an of 0.2 in medium PC1 supplemented with 0.01 g.L⁻ vitamin B12. If indicated ammonium sulfate was replaced by 5.6 g/l ammonium thiosulfate. Spectinomycin was added if necessary at a concentration of 100 mg/l. At an OD600 of 4.5 to 5 extracellular amino acids were quantified by HPLC after OPA/Fmoc derivatization and other relevant metabolites were analyzed using GC-MS after silylation.

TABLE 1

Composition of minimal medium PC1

| Compound | Concentration |
|---|---|
| ZnSO4•7H2O | 0.0040 g·L$^{-1}$ |
| CuCl2•2H2O | 0.0020 g·L$^{-1}$ |
| MnSO4•H2O | 0.0200 g·L$^{-1}$ |
| CoCl2•6H2O | 0.0080 g·L$^{-1}$ |
| H3BO3 | 0.0010 g·L$^{-1}$ |
| Na2MoO4•2H2O | 0.0004 g·L$^{-1}$ |
| MgSO4•7H2O | 1.00 g·L$^{-1}$ |
| Citric acid | 6.00 g·L$^{-1}$ |
| CaCl2 2H2O | 0.04 g·L$^{-1}$ |
| (NH4)2SO4 | 5.00 g·L$^{-1}$ |
| K2HPO4 | 8.00 g·L$^{-1}$ |
| Na2HPO4 | 2.00 g·L$^{-1}$ |
| (NH4)2HPO4 | 8.00 g·L$^{-1}$ |
| NH4Cl | 0.13 g·L$^{-1}$ |
| NaOH 4M | Adjusted to pH 6.8 |
| FeSO4, 7H2O | 0.04 g·L$^{-1}$ |
| Thiamine | 0.01 g·L$^{-1}$ |
| Glucose | 5.00 g·L$^{-1}$ |
| Vitamin B12 (cyanocobalamin) | 0.01 g·L$^{-1}$ |
| Spectinomycine | 0.2 g·L$^{-1}$ |
| MOPS | 5.00 g·L$^{-1}$ |

As can be seen in Table 2, the amount of methionine is increases upon overexpression of cysE; cysE and metH or cysE, metH and altered expression of metF altogether. Enhanced expression of cysM can further increase methionine production. Certain strains produced higher amounts of methionine in the presence of thiosulfate. The highest methionine production is obtained, when cysE, cysM and metH are overexpressed and metF expression is under the control of the Ptrc promoter in the presence of thiosulfate. Isoleucine production is drastically reduced upon expression of cysE and metH, indicating reduced γ-elimination activity. Overexpression of cysM reduces γ-elimination in a strain overexpressing cysE and metH and expressing metF from a heterologous promoter.

TABLE 2

Methionine and isoleucine in mmol/g DW produced in batch culture with sulfate (S) or thiosulfate (T) as sulphur source by strains described above.

| Genotype | meth (mmol/g DW) (S) | meth (mmol/g DW) (T) | iso (mmol/g DW) (S) | iso (mmol/g DW) (T) |
|---|---|---|---|---|
| MG1655 metA*11 ΔmetJ (pME101-thrA*1) | 0.55 | 0.68 | 0.28 | 0.32 |
| MG1655 metA*11 ΔmetJ (pME101-thrA*1-cysE) | 1.02 | 0.86 | 0.15 | 0.23 |
| MG1655 metA*11 ΔmetJ Ptrc-metH: Km (pME101-thrA*1-cysE) | 1.23 | 1.19 | 0.07 | 0.1 |
| MG1655 metA*11 ΔmetJ Ptrc-metH Ptrc-metF: Km (pME101-thrA*1-cysE) | 1.36 | 1.77 | 0.17 | 0.23 |
| MG1655 metA*11 ΔmetJ Ptrc-metH Ptrc-metF Ptrc-cysM (pME101-thrA*1-cysE) | n.d. | 2.04 | n.d. | 0.02 | n.d., not determined

3. Determination of changes in enzyme activities of CysE and MetH

To validate the changes in the expression of cysE and metH expression, the activities of the corresponding enzymes were determined in crude extracts. For the determination of enzyme activities in vitro, E. coli strains were cultured in minimal medium as described above and harvested at mid log phase. Cells were resuspended in cold potassium phosphate buffer and sonicated on ice (Branson sonifier, 70W). After centrifugation, proteins contained in the supernatants we quantified (Bradford, 1976).

For the determination of serine acetyltransferase activity (CysE) 10 µl extract were assayed in 100 mM Potassium phosphate pH 7.5, 4 mM Acetyl-CoA, 30 mM L-serine for 10 minutes at 25° C. Protein was precipitated with acetone and O-acetyl-serine was detected by GC-MS after derivatization with a silylating reagent.

For the determination of vitamin B12-dependent methionine synthase activity (MetH), 100 µl extract were assayed in 100 mM potassium phosphate pH 7.2, 1 mM homocysteine, 0.25 mM methyltetrahydrofolate, 50 µM vitamin B12, 20 µM S-adenosyl-methionine and 25 mM DTT for 10 minutes at 37° C. Protein was precipitated with acetone and the produced methionine was detected by GC-MS after derivatization with a silylating reagent.

As can be seen in Table 3, overexpression of the genes cysE and metH increases the corresponding enzyme activity. Thus the increased activity of these genes leads to increased methionine production.

TABLE 3

Activities in mUI/g DW of serine acetyltransferase (CysE) and methionine synthase (MetH) in methionine producing strains cultivated in the presence of thiosulfate.

| Genotype | CysE | MetH |
|---|---|---|
| MG1655 metA*11 ΔmetJ (pME101-thrA*1) | 65 | 3.2 |
| MG1655 metA*11 ΔmetJ (pME101-thrA*1-cysE) | 453 | 1.2 |
| MG1655 metA*11 ΔmetJ Ptrc-metH(pME101-thrA*1-cysE) | 475 | 12 |
| MG1655 metA*11 ΔmetJ Ptrc-metH Ptrc-metF: Km (pME101-thrA*1-cysE) | 292 | 6.8 |

Validation of Methionine Production Under Fermentation Conditions

Strains that produced substantial amounts of metabolites of interest were subsequently tested under production conditions in 300 ml fermentors (DASGIP) using a fed batch protocol.

For this purpose an 8 hours culture grown in LB medium with 2.5 g/l glucose was used to inoculate an overnight preculture in minimal medium PC1 (see above). Fermentors were filled with 150 ml of minimal medium (B1) and inoculated to a biomass concentration of nearly 0.09 g/l with 1.5 ml concentrated preculture (between 9 and 12 g/l).

TABLE 4

Composition of minimal medium B1

| Compound | Concentration |
|---|---|
| ZnSO4•7H2O | 0.0040 g·L$^{-1}$ |
| CuCl2•2H2O | 0.0020 g·L$^{-1}$ |
| MnSO4•H2O | 0.0200 g·L$^{-1}$ |
| CoCl2•6H2O | 0.0080 g·L$^{-1}$ |
| H3BO3 | 0.0010 g·L$^{-1}$ |
| Na2MoO4•2H2O | 0.0004 g·L$^{-1}$ |
| MgSO4•7H2O | 1.00 g·L$^{-1}$ |
| CaCl2 2H2O | 0.08 g·L$^{-1}$ |
| (NH4)2SO4 | 5.00 g·L$^{-1}$ |
| K2HPO4 | 8.00 g·L$^{-1}$ |
| Na2HPO4 | 2.00 g·L$^{-1}$ |
| (NH4)2HPO4 | 8.00 g·L$^{-1}$ |
| NH4Cl | 0.13 g·L$^{-1}$ |
| Citric acid | 6.00 g·L$^{-1}$ |
| FeSO4, 7H2O | 0.04 g·L$^{-1}$ |
| Thiamine | 0.01 g·L$^{-1}$ |
| Glucose | 5.00 g·L$^{-1}$ |
| PPG | 0.4 mL·L$^{-1}$ |
| Spectinomycine | 0.2 g·L$^{-1}$ |
| Vitamine B12 (cyanocobalamine) | 0.01 g·L$^{-1}$ |
| NaOH 4M | Adjusted to pH 6.8 |

TABLE 5

Minimal medium FB type T1

| Compound | Concentration |
|---|---|
| ZnSO4•7H2O | 0.0040 g·L$^{-1}$ |
| CuCl2•2H2O | 0.0020 g·L$^{-1}$ |
| MnSO4•H2O | 0.0200 g·L$^{-1}$ |
| CoCl2•6H2O | 0.0080 g·L$^{-1}$ |
| H3BO3 | 0.0010 g·L$^{-1}$ |
| Na2MoO4•2H2O | 0.0004 g·L$^{-1}$ |
| MgSO4 | 5.00 g·L$^{-1}$ |
| Citric acid | 6.00 g·L$^{-1}$ |
| (NH4)2SO4 | 8.32 g·L$^{-1}$ |
| Na2SO4 | 8.95 g·L$^{-1}$ |
| (NH4)2S2O3 | 22.32 g·L$^{-1}$ |
| FeSO4, 7H2O | 0.04 g·L$^{-1}$ |
| Thiamine | 0.01 g·L$^{-1}$ |
| Glucose | 500 g·L$^{-1}$ |
| Spectinomycine | 0.2 g·L$^{-1}$ |
| Vitamine B12 (Cyanocobalamine) | 0.01 g·L$^{-1}$ |
| NH4OH 28% | Adjusted to pH 6.0 before thiosulfate addition |

TABLE 6

Minimal medium FB type S

| Compound | Concentration |
|---|---|
| ZnSO4•7H2O | 0.0040 g·L$^{-1}$ |
| CuCl2•2H2O | 0.0020 g·L$^{-1}$ |
| MnSO4•H2O | 0.0200 g·L$^{-1}$ |
| CoCl2•6H2O | 0.0080 g·L$^{-1}$ |
| H3BO3 | 0.0010 g·L$^{-1}$ |
| Na2MoO4•2H2O | 0.0004 g·L$^{-1}$ |
| MgSO4 | 5.00 g·L$^{-1}$ |
| Citric acid | 6.00 g·L$^{-1}$ |
| (NH4)2SO4 | 20.0 g·L$^{-1}$ |
| Na2SO4 | 10.0 g·L$^{-1}$ |
| FeSO4, 7H2O | 0.04 g·L$^{-1}$ |
| Thiamine | 0.01 g·L$^{-1}$ |
| Glucose | 500 g·L$^{-1}$ |
| Spectinomycine | 0.2 g·L$^{-1}$ |
| Vitamine B12 (Cyanocobalamine) | 0.01 g·L$^{-1}$ |
| NH4OH 28% | Adjusted to pH 6.8 |

The temperature of the culture was maintained constant at 37° C. and the pH was permanently adjusted to values between 6.5 and 8, preferentially 6.7 using an NH$_4$OH solution. The agitation rate was maintained at 600 rpm during the batch phase and was increased to up to 1000 rpm at the end of the fed-batch phase. The concentration of dissolved oxygen was maintained at values between 20 and 4%, preferentially 30% saturation by using a gas controller. When the cell mass reached a concentration of 0.9 to 1.2 g/l the fed-batch was started with an initial flow rate between 0.1 and 1.5 ml/h, preferentially 0.43 ml/h and a sigmoidal (24 h) increase up to flow rate values between 0.5 and 5.8 ml/h, preferentially 1.7 ml/h. The precise feeding conditions were calculate by the formula below:

$$Q(t) = p1 + \frac{p2}{1 + e^{-p3(t-p4)}}$$

where Q(t) is the feeding flow rate in mL/h for a batch volume of 150 mL

P1 is between 0.025 and 0.35, preferentially 0.10.
P2 is between 0.400 and 5.600, preferentially 1.100.
P3 is between 0.068 and 0.95, preferentially 0.270.
P4 is between 1.250 and 17.5, preferentially 5.000.

In this case FB medium containing glucose at concentrations between 300 and 800 g/l (preferentially 500 g/L) was used.

When the concentration of biomass had reached values between 20 and 50 g/l (preferentially 35 g/L, between 40 and 80 h) the fermentation was stopped and the extracellular methionine and isoleucine concentrations were determined using HPLC.

TABLE 7

Methionine titers obtained in Fed-batch fermentations of strains overexpressing cysE, and metH or metF under a heterologous promoter or a combination of the three. Ref corresponds to MG1655 metA*11 ΔmetJ. Strains were grown in the presence of thiosulfate (T) or sulfate (S).

| Genotype | Thiosulfate/sulfate | met (mM) | Iso (mM) |
|---|---|---|---|
| Ref + (pME101-thrA*1) | S | 70 mM | 25 mM |
| Ref + (pME101-thrA*1) | T | 94 mM | 35 mM |
| Ref + (pME101-thrA*1-cysE) | S | 74 mM | 2 mM |
| Ref + (pME101-thrA*1-cysE) | T | 101 mM | 0 mM |
| Ref + Ptrc-metH Ptrc-metF: Km (pME101-thrA*1-cysE) | T | 121 mM | 1 mM |

As can be seen in Table 7, enhanced expression of cysE, cysE and metH, cysE, metH and metF under the control of a heterologous promoter or growing the stains in the presence of thiosulfate can significantly increase methionine production. Isoleucine production is significantly reduced by overexpressing cysE and/or metH.

The stain that produced the highest amount of methionine in the 300 mL fermentor was subsequently tested under production conditions in a 2.5 L fermentor (PIERRE GUERIN) using a fed batch protocol.

For this purpose an 8 h culture grown in LB medium with 2.5 g/l glucose was used to inoculate an overnight preculture in minimal medium PC1. Fermentors were filled with 600 ml of minimal medium (B2) and inoculated to a biomass of 0.9 g/l with 6 ml concentrated preculture (between 9 and 12 g/l).

The temperature of the culture was maintained constant at 37° C. and the pH was permanently adjusted to values between 6.3 and 8, preferentially 6.8 using an NH$_4$OH 28% solution. The initial agitation rate was set at 200 rpm during the batch phase and was increased to up to 1200 rpm during the fed-batch phase. The initial airflow rate was set at 40 Nl/h during the batch phase and was increased to up to 250 Nl/h during the fed-batch-phase. The concentration of dissolved oxygen was maintained at values between 20 and 40% saturation, preferentially 30% by increasing the agitation rate and the airflow rate. When the biomass concentration reached 1.2 to 1.5 g/l, the fed-batch was started with an initial flow rate between 0.5 and 4 ml/h, preferentially 1.0 ml/h and an exponential increase (15 h) up to flow rate values between 3 and 35 ml/h, preferentially 0.1 nl/h. At this point, the flow rate was maintained constant for 10 to 45 hours, preferentially 30 h. For the feeding FB type T2 was used (See table 8) containing glucose at concentrations between 300 and 800 g/l, preferentially 750 g/l.

When the concentration of biomass had reached values between 40 and 110 g/l, preferentially 90 g/l the fermentation was stopped and the extracellular methionine concentration was determined using HPLC. The strain MG1655 metA*11 ΔmetJ Ptrc-metH Ptrc-metF (pME101-thrA*1-cysE) produced 169 mM methionine under these conditions.

TABLE 8

Minimal medium FB T2

| Compound | Concentration |
|---|---|
| ZnSO4•7H2O | 0.0040 g · L$^{-1}$ |
| CuCl2•2H2O | 0.0020 g · L$^{-1}$ |
| MnSO4•H2O | 0.0200 g · L$^{-1}$ |
| CoCl2•6H2O | 0.0080 g · L$^{-1}$ |
| H3BO3 | 0.0010 g · L$^{-1}$ |
| Na2MoO4•2H2O | 0.0004 g · L$^{-1}$ |
| MgSO4 | 5.00 g · L$^{-1}$ |
| Citric acid | 6.00 g · L$^{-1}$ |
| K2HPO4, 3H2O | 3.93 g · L$^{-1}$ |
| (NH4)2SO4 | 5.54 g · L$^{-1}$ |
| Na2SO4 | 5.96 g · L$^{-1}$ |
| (NH4)2S2O3 | 33.48 g · L$^{-1}$ |
| FeSO4, 7H2O | 0.04 g · L$^{-1}$ |
| Thiamine | 0.01 g · L$^{-1}$ |
| Glucose | 750 g · L$^{-1}$ |
| Spectinomycine | 0.2 g · L$^{-1}$ |
| Vitamine B12 (Cyanocobalamine) | 0.01 g · L$^{-1}$ |
| NH4OH 28% | Adjusted to pH 6.0 before thiosulfate addition |

TABLE 9

Composition of minimal medium B2

| Compound | Concentration |
|---|---|
| ZnSO4•7H2O | 0.0040 g · L$^{-1}$ |
| CuCl2•2H2O | 0.0020 g · L$^{-1}$ |
| MnSO4•H2O | 0.0200 g · L$^{-1}$ |
| CoCl2•6H2O | 0.0080 g · L$^{-1}$ |
| H3BO3 | 0.0010 g · L$^{-1}$ |
| Na2MoO4•2H2O | 0.0004 g · L$^{-1}$ |
| MgSO4•7H2O | 1.00 g · L$^{-1}$ |
| CaCl2 2H2O | 0.16 g · L$^{-1}$ |
| (NH4)2SO4 | 5.00 g · L$^{-1}$ |
| K2HPO4 | 15.00 g · L$^{-1}$ |
| Na2HPO4 | 2.00 g · L$^{-1}$ |
| (NH4)2HPO4 | 8.00 g · L$^{-1}$ |
| NH4Cl | 0.13 g · L$^{-1}$ |
| Citric acid | 6.00 g · L$^{-1}$ |
| FeSO4, 7H2O | 0.04 g · L$^{-1}$ |
| Thiamine | 0.01 g · L$^{-1}$ |
| Glucose | 5.00 g · L$^{-1}$ |
| PPG | 0.4 mL · L$^{-1}$ |
| Spectinomycine | 0.2 g · L$^{-1}$ |
| Vitamine B12 (cyanocobalamine) | 0.01 g · L$^{-1}$ |
| NaOH 4M | Adjusted to pH 6.8 |

The invention claimed is:

1. A method for producing methionine, derivatives or precursors thereof comprising:
culturing a microorganism modified to enhance production of cysteine, as compared to cysteine production in an unmodified microorganism, in a culture medium comprising a source of carbon and a source of sulfur; and recovering methionine from the culture medium,
wherein said microorganism has a methionine repressor encoded by metJ gene that is deleted or mutated, and has an increased expression of the cysE gene encoding serine acetyltransferase and an increased expression of metH gene encoding methionine synthase, as compared to the expression of the cysE and metH genes in an unmodified microorganism.

2. The method of claim 1, wherein at least one other gene involved in cysteine production is overexpressed, as compared to the expression in an unmodified microorganism, said gene being selected from the group consisting of:

| | |
|---|---|
| cysA | sulfate permease, |
| cysU, cysT | component of sulfate ABC transporter, |
| cysW | membrane bound sulfate transport protein, |
| cysH | adenylylsulfate reductase, |
| cysI | sulfite reductase, alpha subunit, |
| cysJ | sulfite reductase, beta subunit, |
| cysM | O-acetyl-sulfhydrylase, |
| cysZ | sulfate transport, and |
| sbp | Periplasmic sulfate-binding protein. |

3. The method of claim 1, wherein the expression of at least one other gene, which is involved in the production of C1 units and transfer potential onto homocysteine, is increased, as compared to the expression in an unmodified microorganism, and/or driven by a heterologous promoter.

4. The method of claim 3, wherein the at least one other gene, which is involved in production of C1 units and transfer potential onto homocysteine, is selected from the group consisting of:

metE encoding methionine synthase,
metF encoding 5,10-methylenetetrahydrofolate reductase,
glyA encoding serine hydroxymethyltransferase, and
gcvTHP, lpd encoding the glycine cleavage complex.

5. The method of claim 4, wherein expression of metE, metH and/or metF is increased, as compared to the expression in an unmodified microorganism, and/or at least one of the genes is expressed from a heterologous promoter.

6. The method of claim 1, further comprising increasing expression of additional genes involved in production of methionine, as compared to the expression of said additional genes in an unmodified microorganism.

7. The method of claim 1, wherein the sulfur source in the culture medium is sulfate, thiosulfate, hydrogen sulfide, dithionate, dithionite, sulfite or a combination of different sources.

8. The method of claim 7, wherein the sulfur source in the culture medium is sulfate or thiosulfate, or a mixture thereof.

9. The method of claim 1, comprising isolating desired amino acids/ constituents of the fermentation medium and/or biomass optionally remaining in portions or in a total amount (0-100%) in an end product.

10. A method for producing methionine, derivatives or precursors thereof comprising:
culturing a microorganism modified to enhance production of cysteine, as compared to cysteine production in an unmodified microorganism, in a culture medium comprising a source of carbon and a source of sulfur, and recovering methionine from the culture medium,
wherein said microorganism has a methionine repressor encoded by metJ gene that is deleted or mutated, has an increased expression of the cysE gene encoding serine acetyltransferase, and an increased expression of the metH gene encoding methionine synthase, as compared to the expression of cysE and metH genes in an unmodified microorganism, and that expresses a metA allele encoding homoserine succinyltransferase enzyme with reduced feed-back sensitivity to S-adenosylmethionine and/or methionine, as compared feed-back sensitivity of a wild-type enzyme, and a thrA allele encoding homoserine aspartokinase enzyme with reduced feed-back sensitivity to threonine, as compared to feed-back sensitivity of a wild-type enzyme.

11. A method for producing methionine, derivatives or precursors thereof comprising:
   culturing a microorganism modified to enhance production of cysteine, as compared to cysteine production in an unmodified microorganism, in a culture medium comprising a source of carbon and a source of sulfur; and
   recovering methionine from the culture medium,
   wherein said microorganism has a methionine repressor encoded by metJ gene that is deleted or mutated, and has an increased expression of the cysE gene encoding serine acetyltransferase, and an increased expression of the metH gene encoding methionine synthase, and an increased expression of the metF gene encoding 5,10-methylenetetrahydrofolate reductase, as compared to the expression of the cysE, metH and metF genes in an unmodified microorganism, and that expresses a metA allele encoding homoserine succinyltransferase enzyme with reduced feed-back sensitivity to S-adenosylmethionine and/or methionine, as compared to feed-back sensitivity of a wild-type enzyme, and a thrA allele encoding homoserine aspartokinase enzyme with reduced feed-back sensitivity to threonine, as compared to feed-back sensitivity of a wild-type enzyme.

12. A method for producing methionine, derivatives or precursors thereof comprising:
   culturing a microorganism modified to enhance production of cysteine, as compared to cysteine production in an unmodified microorganism in a culture medium comprising a source of carbon and a source of sulfur; and
   recovering methionine from the culture medium,
   wherein said microorganism has an increased expression of the cysE gene encoding serine acetyltransferase, and an increased expression of the metH gene encoding methionine synthase, and an increased expression of the metF gene encoding 5,10-methylenetetrahydrofolate reductase, as compared to the expression of the cysE, metH, and metF genes in an unmodified microorganism, and expresses a metA allele encoding homoserine succinyltransferase enzyme with reduced feed-back sensitivity to S-adenosylmethionine and/or methionine, as compared to feed-back sensitivity of a wild-type enzyme, and a thrA allele encoding homoserine aspartokinase enzyme with reduced feed-back sensitivity to threonine, as compared to feed-back sensitivity of a wild-type enzyme, and has a methionine repressor encoded by metJ gene that is deleted or mutated, and an increased expression of the cysM gene encoding O-acetyl-sulfhydrylase, as compared to the expression of the cysM gene in an unmodified microorganism.

* * * * *

UNITED STATES PATENT AND TRADEMARK OFFICE
CERTIFICATE OF CORRECTION

PATENT NO. : 8,389,250 B2  
APPLICATION NO. : 12/159846  
DATED : March 5, 2013  
INVENTOR(S) : Figge et al.

Page 1 of 1

It is certified that error appears in the above-identified patent and that said Letters Patent is hereby corrected as shown below:

In the Specification

In Column 4

At line 48, please change "CLUSTAL." to -- CLUSTAL W --.

In Column 17

At line 3, please change "4%" to -- 40% --; at line 18, please change "0.10" to -- 0.100 --; and at line 19, please change "1.100" to -- 1.600 --.

Signed and Sealed this
Twenty-fourth Day of September, 2013

Teresa Stanek Rea
*Deputy Director of the United States Patent and Trademark Office*